United States Patent [19]
Lloyd

[11] Patent Number: 5,359,998
[45] Date of Patent: Nov. 1, 1994

[54] MANUAL RESUSCITATOR

[76] Inventor: Lee J. Lloyd, Route 2, Box 121, Micanopy, Fla. 32667

[21] Appl. No.: 965,494

[22] Filed: Oct. 23, 1992

[51] Int. Cl.⁵ ............................................ A61M 16/00
[52] U.S. Cl. .......................... 128/203.11; 128/205.13
[58] Field of Search .................... 128/200.26, 203.11, 128/205.13, 207.14, 207.16

[56] References Cited

U.S. PATENT DOCUMENTS

| | | | |
|---|---|---|---|
| 3,262,446 | 7/1966 | Stoner | 128/205.13 |
| 3,363,833 | 6/1965 | Laerdal | 128/205.13 |
| 4,037,595 | 7/1977 | Elam | 128/205.24 |
| 4,240,417 | 12/1980 | Holerer | 128/912 |
| 4,320,754 | 3/1982 | Watson et al. | 128/205.13 |
| 4,374,521 | 2/1983 | Nelson et al. | 128/205.13 |
| 4,501,271 | 2/1985 | Clifton et al. | 128/205.13 |
| 4,821,715 | 4/1989 | Downing | 128/200.26 |
| 5,029,580 | 7/1991 | Radford et al. | 128/207.14 |
| 5,109,840 | 5/1992 | Daleiden | 128/205.13 |

OTHER PUBLICATIONS

Spearman, Charles B. (1990) "Manual Resuscitators" in Respiratory Therapy Equipment 4:120-138 edited by Stephen MacPherson.

*Primary Examiner*—Edgar S. Burr
*Assistant Examiner*—Aaron J. Lewis
*Attorney, Agent, or Firm*—Saliwanchik & Salinwanchik

[57] ABSTRACT

An improved manual resuscitator is disclosed comprising a lavage port which permits irrigation of patient airways without having to remove a resuscitator from contact with the patient in order to administer irrigating solution. Also disclosed is a method of using the novel resuscitator which is a novel method of lavaging a patient.

12 Claims, 1 Drawing Sheet

MANUAL RESUSCITATOR

BACKGROUND OF THE INVENTION

1. Field of the Invention

The present invention relates generally to the construction of manual resuscitators. The invention particularly relates to the construction of a manual resuscitator which permits administration of irrigation fluids to a patient without having to remove the resuscitator from contact with the patient.

2. Description of Prior Art

Manual resuscitators have been known and widely used for over 35 years. Their purpose is to provide manually applied positive pressure to the airways of a patient. Air, air and oxygen mixtures, or oxygen can be delivered to a patient by means of these resuscitators that can be connected to a face mask or an artificial airway. In one form or another, they all comprise a bag (usually self-inflating) having a bag inlet, an outlet opening, a patient-end opening (which can be connected to a face mask or an artificial airway), and a non-rebreathing valve mechanism which prevents a patient's exhalation from entering the bag. Among the various types of non-rebreathing valve mechanisms which have been used are spring disk, cupped disk, spring ball, diaphragm, duckbill, diaphragm and duckbill, and diaphragm and leaf valve. A more complete description of various types of resuscitators bags which have been commonly used is provided in Spearman, Charles B. [1990] "Manual Resuscitators" in *Respiratory Therapy Equipment* 4th Ed., pp. 120–138, edited by Stephen MacPherson.

Resuscitator bags are commonly used by health care personnel for hyperoxygenation as a prelude to suctioning a patient. Typically, in connection with the procedure a few milliliters of irrigating solution (usually "normal" or "half-normal" saline) is administered in a patient's endotracheal or tracheostomy tube and then impelled into the patient's airway by manually applied positive pressure from the resuscitator. This procedure is commonly referred to as tracheal lavage. Resuscitators of the prior art do not permit administration of the irrigation solution while contact is maintained between the resuscitator and the patient. Unfortunately, administration of the irrigation solution causes a cough reflex in many patients which can result in severe coughing. Since the resuscitator is not in contact with the patient, attached to the endotracheal tube or tracheostomy tube, sputum or pulmonary secretions are frequently coughed out the open end of such tubes, subjecting health care personnel and any others in the vicinity to risk of infection. Also at risk is the patient himself, who by spewing such matter may cause infection of post-surgical or otherwise open wounds on his own body.

The subject invention is an improved manual resuscitator which obviates this serious prior art problem by allowing irrigating solution to be administered and subsequently impelled into a patient's airways without having to remove the manual resuscitator from contact with the patient, and thereby reducing the risk of infection from contact with patient sputum or pulmonary secretions.

SUMMARY OF THE INVENTION

The present invention provides an improved manual resuscitator which comprises a lavage port. The lavage port is disposed between the non-rebreathing valve mechanism and the patient-end opening of the resuscitator. Conveniently, this lavage port permits a health care professional to lavage a patient prior to suctioning by administering irrigating solution and impelling it into a patient's airways without having to remove the resuscitator from contact with the patient.

DETAILED DESCRIPTION OF THE INVENTION

Figure 1:
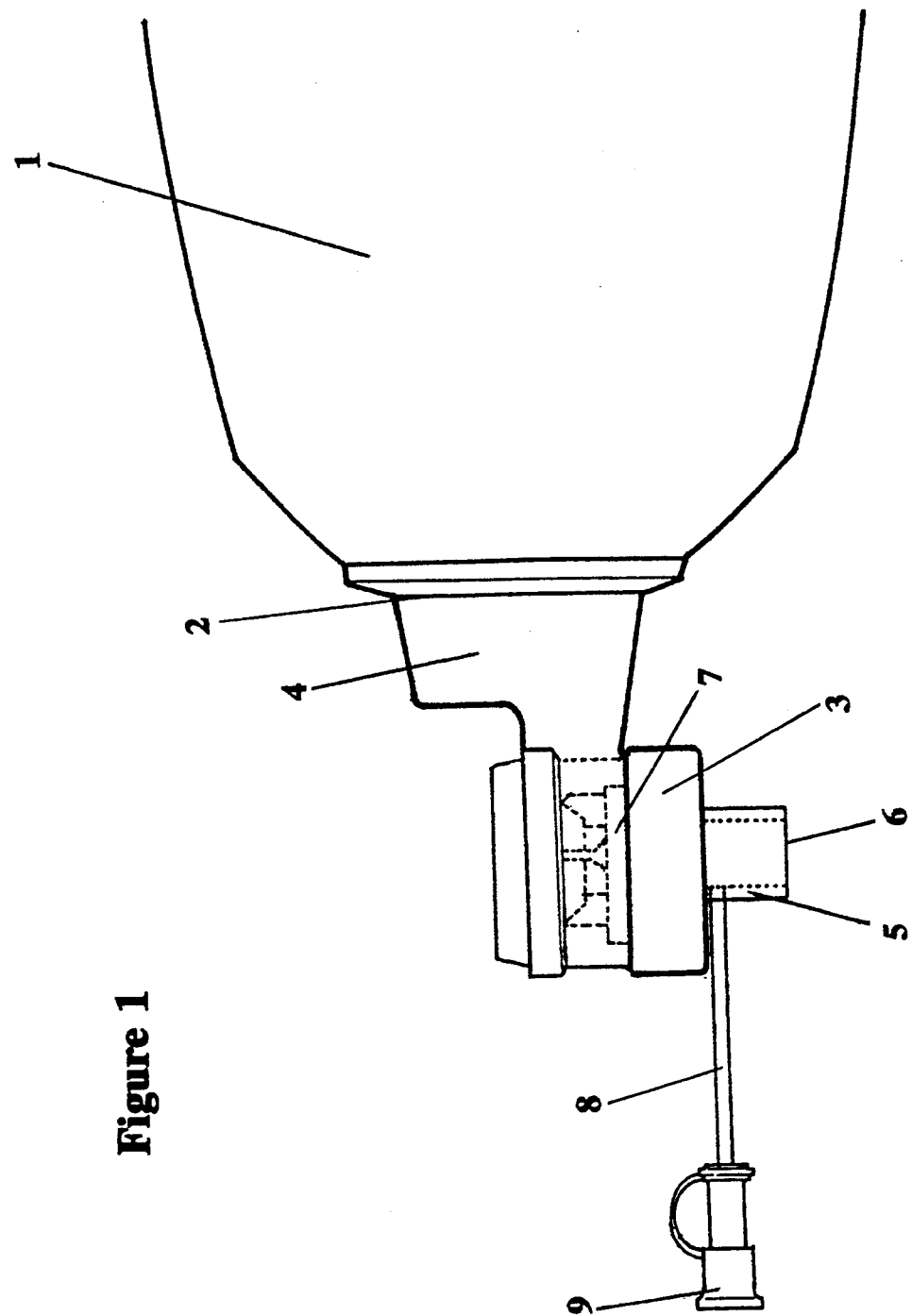
FIG. 1 depicts a standard manual resuscitator having a preferred embodiment of the lavage port comprising a lavage tube and cap.

The apparatus of the invention is conveniently fabricated by conventional and standard methods for preparing manual resuscitators using conventional and standard materials. For example, the bag component of the manual resuscitator may be silicone, rubber, neoprene, or any other standard material which is conventionally employed. The valve housing may be fabricated from conventional polymers such as, for example, polystyrene, polycarbonate, polyurethane, polyethylene, phenolformaldehyde resins, polybutylene, silicone, and the like. Depending on the type of non-rebreathing mechanism, the non-rebreathing valve will be constructed of standard materials well known in the art.

FIG. 1 is an oblique view of the pertinent portion of a manual resuscitator comprising a preferred embodiment of the subject invention. As shown in the illustration of FIG. 1, the manual resuscitator comprises a bag 1, an outlet opening 2 in said bag, and a valve housing 3, having a bag end 4 and a patient end 5. Valve housing 3 is hollow, its interior defining an air passageway extending from an opening in bag end 4 through an opening in patient end 5 (patient-end opening 6), which is shown in FIG. 1. Valve housing 3 is connected at its bag end 4 to outlet opening 2 of bag 1. Non-rebreathing valve mechanism 7 is disposed inside valve housing 3 between the opening in bag end 4 and patient-end opening 6. On compression of bag 1, air is forced through bag outlet opening 2, through the opening in bag end 4 of valve housing 3, through the interior air passage way of valve housing 3 past non-rebreathing valve mechanism 7 and out patient-end opening 6 where the air passes into the patient's airways. This is typically accomplished by means of a face mask, an endotracheal tube, or a tracheostomy tube, any of which can be attached to patient end 5 of valve housing 3. The patient end 5 forms a universal connector with external diameter and internal diameter (as defined by patient end opening 6) dimensions which are standard in the art to conveniently allow attachment of face masks, endotracheal tubes, and tracheostomy tubes which are also standard in the art.

FIG. 1 also depicts a preferred embodiment of lavage port 8, which can be a flexible, substantially cylindrical hollow tube which is open at each end. The internal end of the lavage port 8 projects through the valve housing 3 such that it opens into the interior air passageway at a point disposed between the non-rebreathing mechanism 7 and the patient-end opening 6. In a preferred embodiment, the lavage port 8 may be constructed of polyvinylchloride, silicone, or other standard materials known in the art to be acceptable for its intended purposes. Lavage port 8 may be fixedly connected to valve housing 3 by means of unitary construction, for example, by such techniques of injection molding as are well known in the art. Alternatively, lavage port 8 may be fixedly connected to valve housing 3 during assembly of the manual resuscitator. Also depicted in the preferred embodiment of FIG. 1 is lavage port cap 9, which is attached to the external-end opening of lavage port 8. Lavage port cap 9, when in place covering the external-end opening of lavage port 8, serves to maintain maximum air pressure applied to a patient upon compression of resuscitator bag 1 by minimizing leakage through lavage port 8. Alternative means for closing the external end opening of lavage port 8 are a removable plug, or a one-way valve which permits irrigating solution to be administered from the external-end opening through lavage port 8 and out the internal-end opening of the port into the interior air passageway of valve housing 3, but does not permit significant amounts of air to flow from the internal air passageway of valve housing 3 through lavage port 8 in the opposite direction. In an alternative embodiment, lavage port 8 can be an orifice positioned through valve housing 3 at a point between non-rebreathing valve mechanism 7 and patient-end opening 6, having an external opening on the outside surface of valve housing 3 and an internal opening to the interior air passageway of valve housing 3, and having means for preventing flow of air or other matter from the interior air passageway to the outside through the lavage port 8 as described above.

Conveniently, the internal diameter of lavage port 8 is large enough to accommodate the opened end of unit dose packages of normal saline which are typically used in aerosol therapy (usually 2.5 ml to 5.0 ml), and which are standard in the art (for example, "ARM-A-VIAL", manufactured by Astra Pharmaceutical Products, Inc., Westborough, Mass.). In most cases this will be less than $\frac{1}{4}$-inch inside diameter.

In the preferred embodiment, the improved resuscitator can be placed in contact with a patient via connection of patient-end 5 to an endotracheal tube or a tracheostomy tube which has already been inserted into a patient. Once this contact between resuscitator and patient has been established, it need not be broken for lavaging to take place. In the preferred embodiment, when lavaging is desired, cap 9 may be removed from lavage port 8, irrigating solution may be administered through lavage port 8 into the interior air passageway of valve housing 3 where it is them impelled by compression of resuscitator bag 1 into the patient's airway. In this manner the lavage port enables lavaging to take place without the health care technician having to remove the resuscitator from contact with the patient, thereby avoiding the risk of infection from contact with sputum or pulmonary secretions resulting from the patient's cough reflex reaction to administration of irrigating solution.

Although the foregoing invention has been described in some detail by way of illustration and example, it will be understood that the present invention is not limited to the particular description and specific embodiments described, but rather may comprise a combination of the above elements and variations thereof, many of which will be obvious to those skilled in the art in view of this disclosure. Instead, the invention is limited and defined solely by the following claims.

We claim:

1. In a manual resuscitator comprising a bag having an inlet valve and an outlet opening; a valve housing having a bag end and a patient end, an opening in each end, and defining an interior passageway from said bag-end opening through said patient-end opening, said valve housing being connected at said bag end to said outlet opening; a non-rebreathing valve mechanism disposed inside said valve housing between said bag-end opening and said patient-end opening; the improvement comprising a lavage port having an inside diameter of less than about $\frac{1}{4}$-inch disposed in said valve housing between said non-rebreathing valve mechanism and said patient end opening, wherein said lavage port does not lie on a longitudinal axis extending through said valve housing and out of said patient end opening such that a solution introduced through said lavage port does not pass through said lavage port in a linear route directly along the longitudinal axis extending through said valve housing and out from said patient end opening, and accordingly such that any matter ejected from a patient connected to said patient end opening cannot travel along the longitudinal axis through said patient end opening in a linear route and exit said lavage port without deviating from that longitudinal axis.

2. The manual resuscitator of claim 1 further comprising means for preventing flow of air or other material from the interior air passageway to the outside through said lavage port.

3. The manual resuscitator of claim 2, said means comprising a lavage port cap.

4. The manual resuscitator of claim 2, said means comprising a removable plug.

5. The manual resuscitator of claim 2, said means comprising a one-way valve.

6. A method of introducing a solution into a patient's airway comprising the steps of providing a manual resuscitator comprising a bag having an inlet valve and an outlet opening; a valve housing having a bag end and a patient end, an opening in each end, and defining an interior passageway from said bag-end opening through said patient-end opening, said valve housing being connected at said bag end to said outlet opening; a non-rebreathing valve mechanism disposed inside said valve housing between said bag-end opening and said patient-end opening; a lavage port having an inside diameter of less than about $\frac{1}{4}$-inch disposed in said valve housing between said non-rebreathing valve mechanism and said patient end opening, wherein said lavage port does not lie on a longitudinal axis extending through said valve housing and out of said patient end opening such that a solution introduced through said lavage port does not pass through said lavage port in a linear route directly along the longitudinal axis extending through said valve housing an out of said patient end opening, and accordingly such that any matter ejected from a patient connected to said patient end opening cannot travel along the longitudinal axis through said patient end opening in a linear route and exit said lavage port without deviating from that longitudinal axis;

contacting a patient to whom a solution is desired to be administered with said manual resuscitator;

administering the desired solution through said manual resuscitator without removing said manual resuscitator from contact with the patient; and impelling the solution into the patient's airway by compressing the bag of said manual resuscitator.

7. In a manual resuscitator comprising a bag having an inlet valve and an outlet opening; a valve housing having a bag end and a patient end, an opening in each end, said patient end opening having an internal diameter, and defining an interior air passageway from said bag-end opening through said patient-end opening, said patient end opening having a longitudinal axis extending through the center of said internal diameter and through said valve housing said valve housing being connected at said bag end to said outlet opening; a non-rebreathing valve mechanism disposed inside said valve housing between said bag-end opening and said patient-end opening; the improvement comprising a lavage port having an inside diameter of less than about ¼-inch disposed in said valve housing between said non-rebreathing valve mechanism and said patient end opening, wherein said lavage port does not lie on the longitudinal axis extending through the center of the internal diameter of said patient end opening such that a solution introduced through said lavage port does not pass through said lavage port in a linear route directly along the longitudinal axis through said patient end opening, and accordingly such that any matter ejected from a patient connected to said patient end opening cannot travel along the longitudinal axis through said patient end opening in a linear route and exit said lavage port without deviating from that longitudinal axis.

8. The manual resuscitator of claim 7 further comprising means for preventing flow of air or other material from the interior air passageway to the outside through said lavage port.

9. The manual resuscitator of claim 8, said means comprising a lavage port cap.

10. The manual resuscitator of claim 8, said means comprising a removable plug.

11. The manual resuscitator of claim 8, said means comprising a one-way valve.

12. A method of introducing a solution into a patient's airway comprising the steps of:
providing a manual resuscitator comprising a bag having an inlet valve and an outlet opening; a valve housing having a bag end and a patient end, an opening in each end, said patient end opening having an internal diameter and defining an interior passageway from said bag-end opening through said patient-end opening, said patient end opening having a longitudinal axis extending through the center of said internal diameter and through said valve housing, said valve housing being connected at said bag end to said outlet opening; a non-rebreathing valve mechanism disposed inside said valve housing between said bag-end opening and said patient-opening; a lavage port having an inside diameter of less than about ¼-inch disposed in said valve housing between said non-rebreathing valve mechanism and said patient end opening, wherein said lavage port does not lie on a longitudinal axis extending through the center of the internal diameter of said patient end opening such that a solution introduced trough said lavage port does not pass through said lavage port in a linear route directly along the longitudinal axis through said patient end opening, and accordingly such that any matter ejected from a patient connected to said patient end opening cannot travel along the longitudinal axis through said patient end opening in a linear route and exit said lavage port without deviating from that longitudinal axis;
contacting a patient to whom a solution is desired to be administered with said manual resuscitator;
administering the desired solution through said manual resuscitator without removing said manual resuscitator from contact with the patient; and
impelling the solution into the patient's airway be

UNITED STATES PATENT AND TRADEMARK OFFICE
CERTIFICATE OF CORRECTION

PATENT NO. : 5,359,998

DATED : November 1, 1994

INVENTOR(S) : Lee J. Lloyd

It is certified that error appears in the above-indentified patent and that said Letters Patent is hereby corrected as shown below:

Column 4, line 50: Delete "housing an out of" insert --housing and out of--

Column 5, line 3: Delete "housing said" insert --housing, said--

Column 6, line 12: Delete "patient-opening;" insert --patient-end opening;--

Column 6, line 19: Delete "trough" insert --through--

Column 6, line 33: Delete "be" insert --by--

Signed and Sealed this

Seventh Day of February, 1995

Attest:

BRUCE LEHMAN

Attesting Officer

Commissioner of Patents and Trademarks